United States Patent [19]

Bauer

[11] Patent Number: 4,835,085
[45] Date of Patent: May 30, 1989

[54] 1,2-NAPHTHOQUINONE DIAZIDE SULFONYL ESTER COMPOUND WITH LINKING BENZOTRIAZOLE GROUPS AND LIGHT-SENSITIVE COMPOSITION WITH COMPOUND

[75] Inventor: Sigrid Bauer, Paudex, Switzerland

[73] Assignee: Ciba-Geigy Corporation, Ardsley, N.Y.

[21] Appl. No.: 105,379

[22] Filed: Oct. 7, 1987

[30] Foreign Application Priority Data

Oct. 17, 1986 [CH] Switzerland .................. 4156/86

[51] Int. Cl.$^4$ .................. G03C 1/54; C07C 113/00
[52] U.S. Cl. .................. 430/192; 430/165; 430/189; 430/190; 430/193; 534/556
[58] Field of Search ......... 430/190, 189, 165, 193, 430/192; 534/556

[56] References Cited

U.S. PATENT DOCUMENTS

| | | | |
|---|---|---|---|
| 2,907,655 | 10/1959 | Schmidt et al. | 430/193 |
| 3,046,111 | 7/1962 | Schmidt | 96/33 |
| 3,046,124 | 7/1962 | Schmidt | 430/192 |
| 3,248,220 | 4/1966 | Van Rhijn | 430/178 |
| 3,531,414 | 9/1970 | Randell et al. | 252/152 |
| 4,104,070 | 8/1978 | Moritz et al. | 96/36 |

FOREIGN PATENT DOCUMENTS 732294  5/1980  U.S.S.R. .

Primary Examiner—Charles L. Bowers, Jr.
Attorney, Agent, or Firm—Luther A. R. Hall; JoAnn Villamizar

[57] ABSTRACT

Compounds of the general formula (I) or (II)

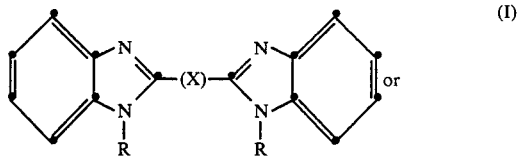

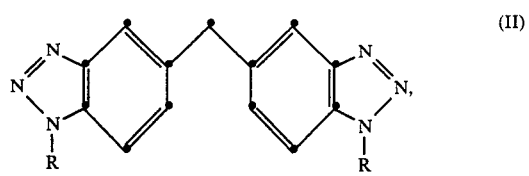

in which R is 1,2-naphthoquinone-2-diazide-4- or -5-sulfonyl and X is a straight-chain or branched $C_1$–$C_{12}$-alkylene group, which is unsubstituted or mono- or disubstituted by OH group or is —CH=CH—, are suitable as the light-sensitive component in photoresist materials. Both positive and negative images can be prepared with light-sensitive mixtures containing these compounds and a binder.

6 Claims, No Drawings

1,2-NAPHTHOQUINONE DIAZIDE SULFONYL ESTER COMPOUND WITH LINKING BENZOTRIAZOLE GROUPS AND LIGHT-SENSITIVE COMPOSITION WITH COMPOUND

The present invention relates to novel o-naphthoquinone-diazides, to light-sensitive mixtures containing these compounds, a process for producing a positive resist image and to a process for producing a negative resist image by image reversal.

U.S. Pat. No. 3,046,111 has disclosed reaction products of hydroxy-naphthoimidazoles with naphthoquinone-diazide-sulfonic acid (chloride) as the light-sensitive component in positive-working photoresist materials. In a positive resist system, the light-sensitive material is modified on exposure in such a way that it becomes soluble in the subsequent developing step. The exposed areas of the resist film are removed on developing, and the free unprotected areas on the substrate surface correspond to the transparent areas on the photo mask. In Soviet Patent Specification No. 732,294, poly-(benzimidazolo-o-naphthoquinone-diazides) are described which give positive images, but no negative images.

A process for producing a negative resist image, using a positive resist material which contains a 1-hydroxy-2-alkylimidazoline, is known from U.S. Pat. No. 4,104,070. A photoresist, the exposed areas of which are insoluble in a suitable developer, whereas the unexposed resist areas are dissolved away by the developer, is termed negative. According to U.S. Pat. No. 4,104,070, the "image reversal" when using a positive material is effected by heating the photoresist layer after the imagewise exposure for a sufficient time to a suitable temperature, subsequently exposing its full area and then developing it.

The present invention relates to novel light-sensitive o-naphthoquinone-diazides of the formula (I) or (II)

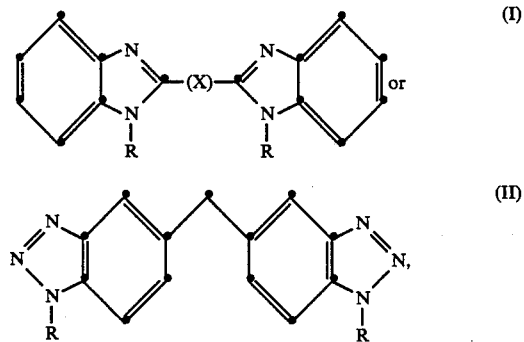

in which R is 1,2-naphthoquinone-2-diazide-4- or -5-sulfonyl and Xi is a straight-chain or branched $C_1$–$C_{12}$-alkylene group which is unsubstituted or mono- or disubstituted by OH groups, or is —CH=CH—.

Examples of groups X are methylene, ethylene, 1,3-propylene, 2,2-propylidene, 1,4-butylene, hexamethylene, octamethylene, dodecamethylene, 2-hydroxy-1,3-propylene or 2,4-dihydroxyhexamethylene. $C_1$–$C_8$-Alkylene groups are preferred.

The compounds of the formula (I) or (II) are prepared in a known manner, for example by reacting the corresponding compounds of the formula (I) or (II), in which R is hydrogen (I* or II* respectively), with approximately the stoichiometric quantity of the sulfonic acid chloride of 1,2-naphthoquinone-diazide, preferably in inert organic solvents in the presence of a base. The sulfonic acid group is here in the 4- or 5-position. A suitable solvent is, for example, dioxane to which dimethylformamide can be added in some cases. Of course, other solvents can also be used for this reaction. The bases employed as acid acceptors are, for example, alkali metal hydroxides or carbonates, pyridine or triethanolamine. The reaction proceeds smoothly at relatively low temperatures, for example 20°–40° C. If desired, the compounds of the formula (I) or (II) can be purified in a known manner, for example by recrystallization or reprecipitation. Methods of this type are described for example, in U.S. Pat. No. 3,046,111 or in O. Süs et al., Angew. Chem. 74, 985 (1962) and in the literature references cited therein. However, the compounds can also be used as such after precipitation, filtering off and drying.

The N-heterocyclic compounds of the formula (I), in which R is hydrogen and which are used as the starting materials, are known. Their preparation is described, for example, in Ann. 599, 44 et seq. (1956). The compound of the formula (II), in which R is hydrogen which is also used as a starting material, is likewise known and has been disclosed, for example, in U.S. Pat. No. 3,531,414.

The present invention also relates to mixtures which contain the novel compounds of the formula (I) or (II). These contain a polymeric water-insoluble resinous binder which dissolves in the solvents used for the mixture according to the invention and is soluble or at least swellable in aqueous alkalies or trialkylammonium compounds.

The novolak condensation resins, well established in many positive copying materials based on naphthoquinone-diazides, have also provded to be particularly useful and advantageous as an additive in the mixtures according to the invention with the novel naphthoquinone-diazide-sulfonic acid amides. They promote the sharp differentiation between the exposed and unexposed image elements on development, especially the more highly condensed resins with substituted phenols, for example cresols, as the formaldehyde condensation partner. Other binders, which are soluble or swellable in alkali, are natural resins such as shellac and colophony, and synthetic resins such as copolymers of styrene and maleic anhydride or copolymers of acrylic acid or methacrylic acid, especially with acrylate or methacryate esters.

The nature and quantity of the alkali-soluble resin can vary depending on the intended use; contents of between 95 and 50% by weight, and especially 90–60% by weight, in total solids are preferred. In addition, numerous other resins, for example additive resins which contain acid groups or also neutral additive resins, can also be included. Epoxides and vinyl polymers such as polyvinyl acetates, polyacrylates, polyvinyl acetals, polyvinyl ethers, polyvinylpyrrolidones and the copolymers of the monomers on which they are based are suitable. The most advantageous proportion of these resins depends on the technological requirements and on their effect on the development conditions, and it is in general not more than 20% by weight of the alkali-soluble resin. For special requirements, such as flexibility, adhesion, gloss, colouration and colour change etc., the light-sensitive mixture can additionally also contain small amounts of substances such as polyglycols, cellulose derivatives such as ethylcellulose, wetting agents, dyes, flow agents, fillers, adhesion promoters, plasticizers and highly disperse pigments as well as UV absorbers, if required. The addition of organic acids or acid donors, i.e. compounds which release acids under the action of actinic radiation, should also be singled out in particular.

For coating a suitable carrier, the mixtures are generally dissolved in a solvent. The choice of solvents should be matched to the envisaged coating process, the layer thickness and the drying conditions. Suitable solvents for the mixture according to the invention are ketones such as methyl ethyl ketone, chlorinated hydrocarbons, such as trichloroethylene and 1,1,1-trichloroethane, alcohols such as n-propanol, ethers such as tetrahydrofuran, alcohol ethers such as ethylene glycol monoethyl ether, and esters such as butyl acetate. Mixtures can also be used which, for special purposes, can also contain solvents such as acetonitrile, dioxane, cyclohexanone or dimethylformamide. In principle, all solvents can be used which do not irreversibly react with the layer components. Partial ethers of glycols, especially ethylene glycol monoethyl ether, are particularly preferred.

The light-sensitive mixtures generally contain 2–35% by weight and especially 7–20% by weight of the sensitizer of the formula (I) or (II), relative to total solids.

The compositions according to the invention are outstandingly suitable as coating agents for substrates of any type, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co, and Si, $SiO_2$ or silicon nitride, to which an image to be applied by imagewise exposure. The present invention also relates to the coated substrates.

Moreover, the invention relates to a process for producing positive images, which comprises the following working steps:
coating a substrate with a radiation-sensitive composition as defined above,
exposing the coated substrate to a predetermined pattern of actinic radiation and
developing the exposed substrate.

The exposure of the coated substrates can be carried out, for example, by applying a solution or suspension of the composition uniformly to a substrate by means of known coating processes, for example by whirler-coating, dipping, knife-coating, curtain-coating methods, brushing, spraying and reverse roller-coating. It is also possible to apply the light-sensitive layer to a temporary, flexible support and then to coat the final substrate, for example a copper-laminated circuit board, by layer transfer via lamination.

The quantity applied (layer thickness) and the nature of the substrate (support) depend on the desired field of application. It is a particular advantage that the compositions according to the invention can be employed in widely variable layer thicknesses.

Possible fields of application of the compositions according to the invention are the use as photoresists for electronics (electroplating resist, etch resist), the preparation of printing plates, such as offset printing plates, for half-tone gravure printing and web printing, and also for the preparation of screen printing formes, the use in chemical milling or the use as microresist in the production of integrated circuits.

The possible supports and processing conditions of the coated substrates are correspondingly diverse.

For example, polyester or cellulose acetate films or plastic-coated papers are used for the photographic recording of information; specially treated aluminium is used for offset printing formes, and copper-coated laminates are used for the production of printed circuits. Si-wafers are used as the carrier material in integrated circuits.

After coating, the solvent is as a rule removed by drying, and the result is a layer of the photoresist on the carrier.

After the imagewise exposure of the material, carried out in the usual way, the exposed areas of the photoresist are removed by dissolving them in a developer.

Aqueous alkaline solutions are particularly preferred as the developer. These include especially aqueous solutions of alkali metal silicates, phosphates and hydroxides, and of trialkylammonium compounds. If appropriate, minor quantities of wetting agents and/or organic solvents can also have been added to these solutions.

Typical organic solvents which can be added to the developer liquids are those which are miscible with water, for example 2-ethoxyethanol or acetone, and mixtures of two or more of these solvents.

The term "exposure to a predetermined pattern of actinic radiation" comprises both exposure through a photo mask containing a predetermined pattern, for example a transparency, and exposure by a laser beam which is moved, for example under computer control, across the surface of the coated substrate and produces an image in this way.

The light sensitivity of the compositions according to the invention ranges as a rule from the UV region (about 250 nm) up to about 600 nm and thus covers a very wide range. A large number of the most diverse types of light sources are therefore used. Both point light sources and two-dimensionally extended radiation sources (lamp carpets) are suitable. Examples are: carbon arc lamps, xenon arc lamps, mercury vapour lamps, if appropriate doped with metal halides (metal halogen lamps), fluorescent lamps, incandescent argon lamps, electronic flash lights and photographic flood lights. The distance between the lamps and the image material according to the invention can vary depending on the application and lamp type or intensity, for example between 2 cm and 150 cm. Laser light sources, for example argon ion lasers or krypton ion lasers with strong emission lines (Ar laser) at 457, 476, 488, 514 and 528 nm, are particularly suitable. In this type of exposure, a photo mask in contact with the photopolymer layer is no longer necessary; the controlled laser beam writes directly on the layer. In this case, the high sensitivity of the materials according to the invention is very advantageous and allows high writing speeds at relatively low intensities. Using this method, printed circuits in the electronics industry, lithographic offset printing plates or relief printing plates as well as photographic image-recording materials can be produced.

If appropriate, the light-sensitive compositions can also contain sensitizers, in order to enhance the spectral sensitivity in a certain region of the electromagnetic spectrum.

The invention therefore also relates to the use of the compositions, as defined above, as positive photoresists for the preparation of positive-working copying layers which serve, for example, for the preparation of integrated circuits, etch resists, offset printing plates, colour test films, stencils, nameplates and the like, and of positive-working dry resist films.

Compared with conventional systems, the use, according to the invention, of the o-naphthoquinone-diazides has especially the following advantages: the o-naphthoquinone-diazides according to the invention confer improved developer resistance on the layers prepared with them and increase the storage stability of solutions and layers. In addition, it has been found that substrate surfaces, which contain copper or oxide or have been treated with hexamethyldisilazane, show better wetting with the novel coating solutions and give surfaces which are free of striations. The developability of the copying layer can be adjusted to any desired developer by the choice of the light-sensitive component.

A special feature is the possibility of image reversal. This is understood to mean that it is possible to obtain a negative resist image by using the positive resist material described above. It is easier for the user of resist solutions, if the resists allow an image reversal, since otherwise the resist solutions must first be modified by suitable additions, which is involved and uneconomical and can also adversely affect the long-term stability of the resist solution.

In image reversal, the photoresist layer is heated, after imagewise exposure, for a sufficient time to a sufficiently high temperature, and the full area of the layer is then exposed and developed. In an advantageous embodiment of the invention, the heating is taken to 100°-130° C., especially to 110°-120° C., for 3 to 20 minutes, especially for 5 to 10 minutes.

The development can be carried out by means of the alkaline developers described above. This process gives a negative resist image which is superior to the resist images produced by conventional negative resist materials with respect to resolution and blemishes.

The present invention therefore also relates to a process for producing negative images, which comprises the following working steps:
coating a substrate with a radiation-sensitive mixture as defined above,
exposing the coated substrate to a predetermined pattern of actinic radiation,
heating the coated substrate,
exposing the full area of the coated substrate to actinic radiation, and
developing the exposed substrate.

EXAMPLE 1

25 g (0.1 mol) of 5,5'-methylene-bis-benzotriazole are dissolved in a mixture of 200 ml of dioxane and 100 ml of water. A solution of 54 g (0.2 mol) of 1,2-naphthoquinone-2-diazide-5-sulfochloride in 250 ml of dioxane is added thereto. 250 ml of 10% soda solution are then added dropwise with vigorous stirring, the temperature rising to 32°-37° C. (Duration of the addition 2-3 hours). 2500 ml of water are then added to the still warm solution, the reaction product precipitating. After cooling, the compound is filtered off with suction, thoroughly washed with water and dried at room temperature.

The yellow-brown quinone-diazide starts to decompose slowly at 125° C.

EXAMPLE 2

Analogously to the method described in Example 1, 274 g (1 mol) of 1,3bis-(2'-benzimidazolyl)-propane and 485 g (2 mol) of 1,2-naphthoquinone-2-diazide-5-sulfonic acid chloride are reacted in dioxane. The product thus obtained starts to decompose at 148° C.

EXAMPLES 3-9

The following reaction products of the formula (I) were prepared as described in Example 1, 2 mol of 1,2-naphthoquinone-2-diazide-5-sulfonic acid chloride being used in each case per mol of benzimidazole compound:

| Example | X in Formula (I) | starts to decompose at |
|---|---|---|
| 3 | —(CH$_2$)$_8$— | 148° C. |
| 4 | —(CH$_2$)$_4$— | 149° C. |
| 5 | —(CH[OH])$_2$— | 205° C. |
| 6 | —CH=CH— (cis) | 135° C. |
| 7 | —CH=CH— (trans) | 146° C. |
| 8 | —CH$_2$— | 205° C. |
| 9 | —(CH$_2$)$_6$— | 141° C. |

The reaction products obtained in accordance with Examples 1 to 9 can be used as such without further purification after precipitation, filtering off with suction and drying.

EXAMPLE 10

A coating solution is prepared from:
4.33 parts by weight of a poly-(p-vinylphenol), Resin M ® from Maruzen Oil,
0.50 part by weight of an epoxide resin of epoxy value 2.0–2.2,
1.00 part by weight of the reaction product according to Example 2,
0.045 part by weight of crystal violet (Colour Index No. 42 555) and
15.60 parts by weight of a solvent mixture of ethylglycol, ethylglycol acetate and methyl ethyl ketone (in a ratio of 2:2:1)
and applied by means of a wire draw bar to electrochemically roughened aluminium. (Dry layer thickness about 2 μm.)

The light-sensitive layer is exposed for 6 seconds with a 5 kW metal halide lamp under a photographic test original which, inter alia, contains a 21-step grey wedge from Stouffer, a UGRA offset test wedge 1982 and a positive screen image, and is developed with developer A, consisting of
40.0 parts by weight of anhydrous Na$_3$PO$_4$,
20.0 parts by weight of sodium metasilicate.5H$_2$O and
960.0 parts by weight of deionized water
in a rocking bath.

This gives a contrast-rich image on a fog-free background.

If image reversal is desired, the procedure is as follows:

The light-sensitive layer is first exposed for 6 seconds as already described above, then heated at 120° C. for 5 minutes, subsequently exposed for 10 seconds across the whole area and finally developed with developer A to give a complementary image of the original used.

If the above light-sensitive compound in the above coating solution is replaced by the reaction product of 1 mol of 1,6-bis-(2'-benzimidazolyl)-hexane and 2 mol of 1,2-naphthoquinone-2-diazide-5-sulfochloride (according to Example 9), the same good results are obtained. However, it is advisable to dilute developer A 1:1 with water.

EXAMPLE 11

A coating solution is prepared from 10.50 parts by weight of a cresol/formaldehyde novolak having a softening point of 110°-120° C.,
1.25 parts by weight of the reaction product according to Example 3,
0.09 part by weight of crystal violet (Colour Index No. 42,555) and
35.60 parts by weight of a solvent mixture of ethylglycol, ethylene glycol acetate and methyl ethyl ketone (in a ratio of 2:2:1)
and applied by means of a wire draw bar to mechanically brushed aluminium. Exposure as described in Example 10 and development with developer A are then carried out. The image thus obtained is perfect.

Image reversal by means of the process steps described in Example 10 is also possible in this case. This gives a fog-free complementary image of the original used.

Equally good results are obtained when the above light-sensitive compound is replaced by the reaction product according to Example 2.

If the reaction products according to Example 6 or 9 are used as the light-sensitive compounds and the procedure is in other respects as described in Example 2, qualitatively high-grade positive and negative images of the test original used are obtained. For development, developer A should be diluted with water in a ratio of 1:1.

EXAMPLE 12

A coating solution is prepared from
6.40 parts by weight of a cresol/formaldehyde novolak having a softening point of 110°-120° C.,
0.20 part by weight of a polyvinyl acetal with about 70% of vinyl acetal units, 24–27% of vinyl alcohol units and 1% of vinyl acetate units,
1.00 parts by weight of naphthoquinone-diazide according to Example 1,
0.12 part by weight of 1,2-naphthoquinone-2-diazide-4-sulfonic acid chloride,
0.06 part by weight of crystal violet (Colour Index No. 42,555) and
20.00 parts by weight of the solvent mixture described in Example 1,
and applied to an insulating plate laminated with a 35 μm thick copper foil and dried.

For imaging, the light-sensitive layer is exposed for 6 seconds with a 5 kW metal halide lamp under a line original and developed with a developer consisting of
5.3 parts by weight of sodium metasilicate.9H$_2$O,
3.4 parts by weight of trisodium phosphate.12H$_2$O and
0.3 part by weight of sodium dihydrogen phosphate in
91.0 parts by weight of deionized water.

The plate is etched with a commercially available Fe(III) chloride etch, to which the image areas are resistant.

EXAMPLE 13

A coating solution consisting of
10.50 parts by weight of the novolak described in Example 11,
1.00 part by weight of a brominated epoxy resin of an epoxy value of 2.0–2.2 and a bromine content of about 21.2%,
1.00 part by weight of a styrene/maleic anhydride copolymer having a mean molecular weight of 10,000 and an acid number of 190,
1.25 parts by weight of the reaction product according to Example 3,
0.09 part by weight of crystal violet and
35.60 parts by weight of the solvent mixture described in Example 2,
is applied to mechanically brushed aluminium, and the layer is dried and then exposed for 6 seconds with a 5 kW metal halide lamp under a photographic original.

Development is carried out with a solution of
50.0 parts by weight of sodium metasilicate.5H$_2$O and
2.5 parts by weight of sodium oxide in 1000.0 parts by weight of deionized water.

The plate is then washed off with water, fixed by wiping with 1% phosphoric acid and preserved with a solution of gum arabic.

The plate thus prepared is suitable for offset printing and has an extremely long life.

Image reversal corresponding to the processing steps in Example 2 gives equally good results.

EXAMPLE 14

7 coating solutions (I–VII) are prepared from
21.00 parts by weight of the novolak described in Example 11,
2.00 parts by weight of the epoxide resin described in Example 10,
2.00 parts by weight of a methyl methacrylate/methacrylic acid copolymer having an acid number of 155 and a mean molecular weight of 160,000,
2.50 parts by weight of a reaction product according to Examples 2, 4, 6, 7, 8 and 9,
0.18 part by weight of crystal violet and
71.20 parts by weight of the solvent mixture described in Example 1.

For producing positive or negative images, the solution is applied, as described in Example 2, in a first test series to brushed aluminium and in a second test series to copper-laminated base material, dried and exposed. A suitable developer is the commercial product Kodak micro positive developer ®809, diluted with water in a ratio of 1:1. Qualitatively perfect images are obtained in this way.

EXAMPLE 15

The procedure for producing microelectronic circuit elements is as follows:

A coating solution is prepared from
10.50 parts by weight of the novolak described in Example 11,
2.00 parts by weight of the epoxide resin described in Example 10,
0.60 part by weight of 5,5'-methylene-bis-benzotriazole,
1.25 parts by weight of the naphthoquinone-diazide according to Example 1 and
40.84 parts by weight of a solvent mixture of ethylglycol and ethylglycol acetate (1:1),
filtered through a 0.2 μm filter and applied by whirler-coating to a silicon wafer which has been provided with a 0.2 μm thick SiO$_2$ layer and coated with hexamethyldisilazane as an adhesion promoter. The wafer is then dried for 10 minutes at 90° C. in a circulating-air oven, then cooled and conditioned at 23° C. and 40–50% relative atmospheric humidity for exposure. The layer thickness is 1.2 μm. The exposure is carried out for 6 seconds in a wafer contact exposure apparatus with a 200 Watt Hg high-pressure lamp. The test original used is a commercially available chromium mask with highly resolved line patterns.

Development is carried out with Microposit ®303 from Shipley, which was diluted for this purpose with water in a ratio of 1:4.

The product is then washed with water and blown dry with nitrogen.

The resolution of 2 μm (for lines of corresponding width and spacing).

What is claimed is:

1. A compound of the general formula (I) or (II)

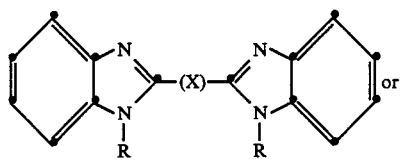 (I)

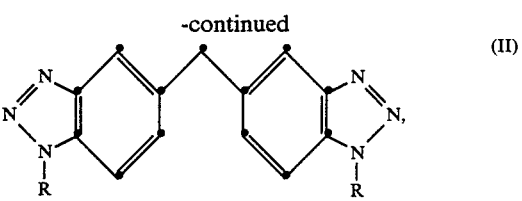 (II)

in which R is 1,2-naphthoquinone-2-diazide-4- or -5-sulfonyl and X is a straight-chain or branched $C_1$–$C_{12}$-alkylene group which is unsubstituted or mono- or di-substituted by OH groups, or is —CH=CH—.

2. A compound according to claim 1, of the formula (I) wherein X is a $C_1$–$C_8$-alkylene group.

3. A radiation-sensitive composition, comprising a radiation-sensitive compound of the formula (I) or (II) according to claim 1 in admixture with a binder wherein said compound and said binder are together in sufficient quantity amounts to produce a resist image.

4. A radiation-sensitive composition according to claim 3, wherein a phenolic resin is the binder.

5. A radiation-sensitive composition according to claim 3, additionally comprising an epoxide resin.

6. A radiation-sensitive composition according to claim 3, containing 2–35% by weight of a compound of the formula (I) or (II) as based on the total weight of the composition.

* * * * *